United States Patent
Carrez et al.

(10) Patent No.: US 8,603,048 B2
(45) Date of Patent: Dec. 10, 2013

(54) CONNECTOR FOR A ESTABLISHING A FLUID COMMUNICATION CONTROLLED BY A VALVE ESSENTIALLY USED IN THE FIELD OF MEDICINE

(75) Inventors: Jean-Luc Carrez, Ecouen (FR); Valery Dalle, Gouvieux (FR); Pierrick Guyomarc'h, Ermont (FR); Jean-Max Huet, Clichy (FR)

(73) Assignee: Vygon, Ecouen (FR)

( * ) Notice: Subject to any disclaimer, the term of this patent is extended or adjusted under 35 U.S.C. 154(b) by 190 days.

(21) Appl. No.: 12/521,812

(22) PCT Filed: Jan. 3, 2008

(86) PCT No.: PCT/EP2008/050040
§ 371 (c)(1),
(2), (4) Date: Jun. 30, 2009

(87) PCT Pub. No.: WO2008/081027
PCT Pub. Date: Jul. 10, 2009

(65) Prior Publication Data
US 2010/0030163 A1     Feb. 4, 2010

(30) Foreign Application Priority Data

Jan. 3, 2007 (FR) .................................. 07 00022

(51) Int. Cl.
*A61M 5/14*     (2006.01)
(52) U.S. Cl.
USPC .......................................... 604/256; 604/246

(58) Field of Classification Search
USPC ................................ 604/256, 533–284, 82–29
See application file for complete search history.

(56) References Cited

U.S. PATENT DOCUMENTS

| 5,474,544 | A | * | 12/1995 | Lynn ............................. 604/537 |
| 5,814,024 | A | * | 9/1998 | Thompson et al. ........... 604/246 |
| 6,068,011 | A | | 5/2000 | Paradis |
| 6,428,520 | B1 | | 8/2002 | Lopez et al. |
| 2005/0151105 | A1 | | 7/2005 | Ryan et al. |

FOREIGN PATENT DOCUMENTS

WO         03018105 A1     3/2003

* cited by examiner

Primary Examiner — Kevin C Sirmons
Assistant Examiner — Phillip Gray
(74) Attorney, Agent, or Firm — Levine & Mandelbaum

(57) ABSTRACT

According to the invention, the spring-effect deformation capacity of the valve (5) essentially relates to the plug (Sa) and to an intermediate valve portion (5c) between the plug (Sa) and a tubular gap (6). The valve (5) and the fixed end piece (3) are conformed so that the valve can be permanently tightened on the fixed end piece without forming a significant dead volume in said gap independently from the deformation of the valve, and so that the valve can be maintained on the fixed end piece (3) without any flexion under the action of the mobile end piece. The slot (9) of the valve includes a moulded proximal slot (9A) followed by a pierced distal slot (9B) for communication between the moulded slot and said gap when the slot is open. Application in medical fluid connectors.

7 Claims, 5 Drawing Sheets

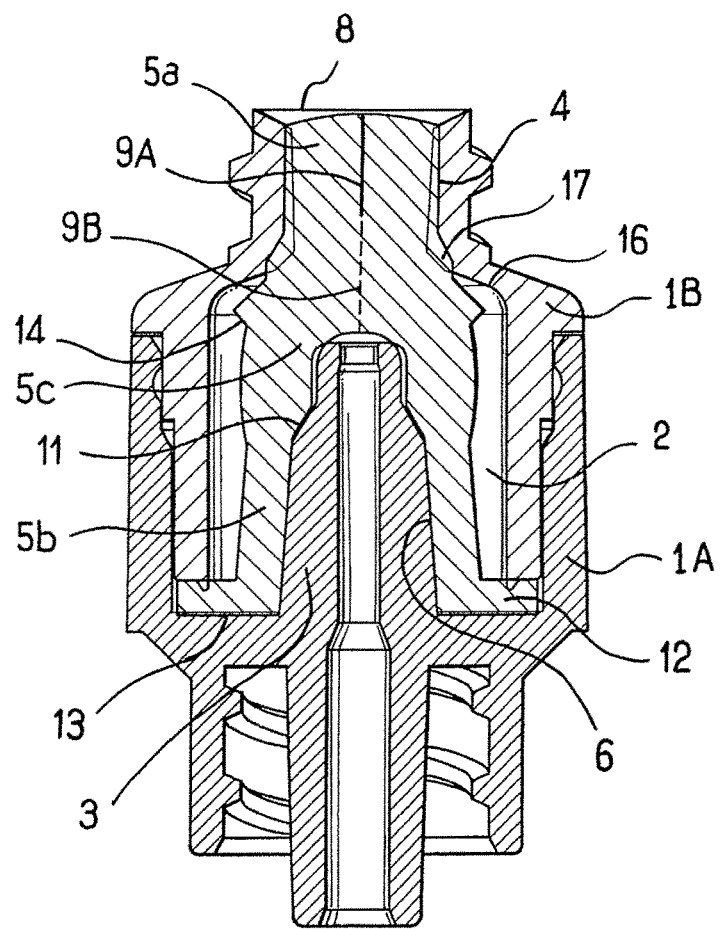
FIG_1

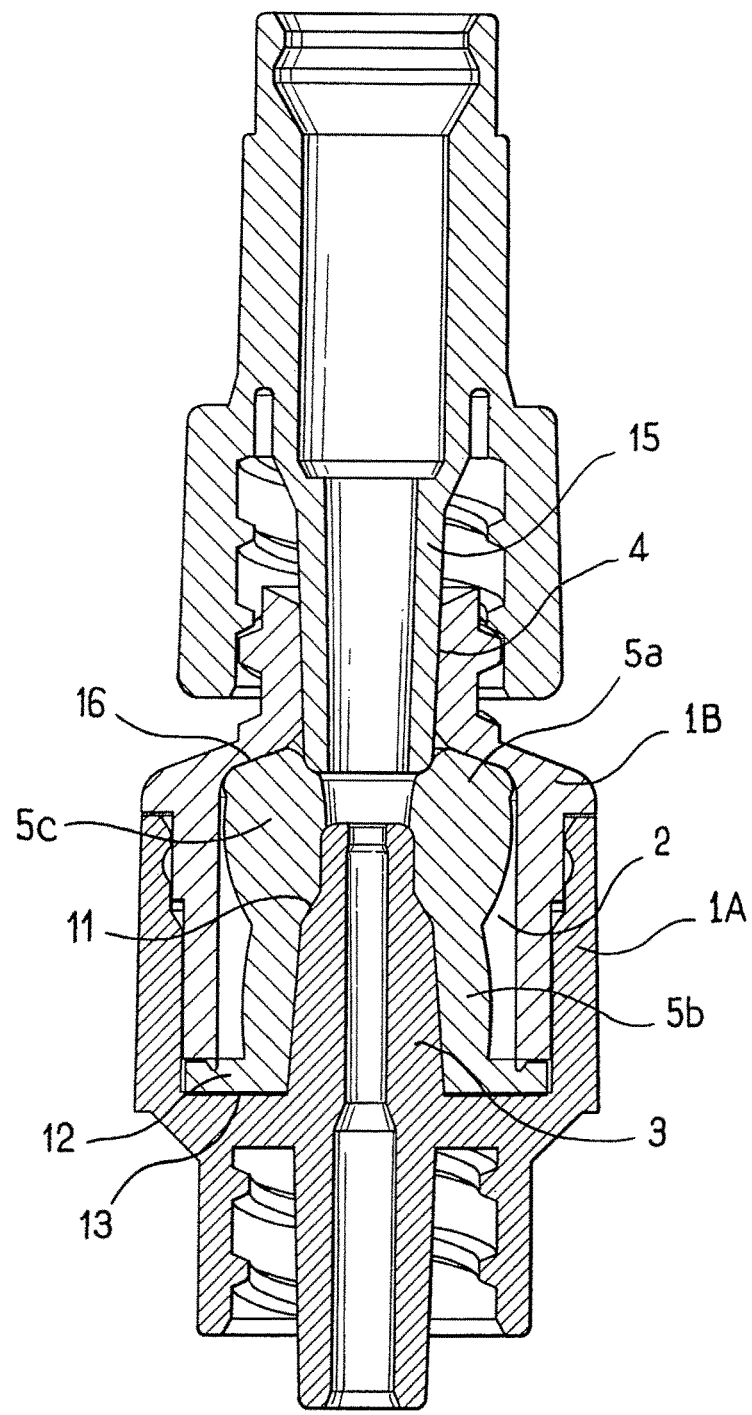
FIG_2

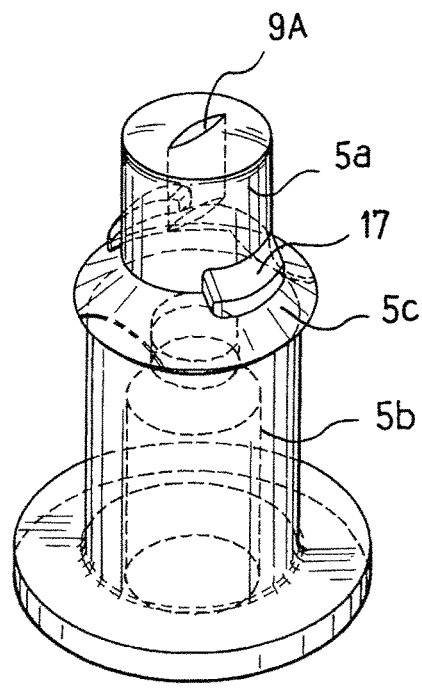
FIG_3
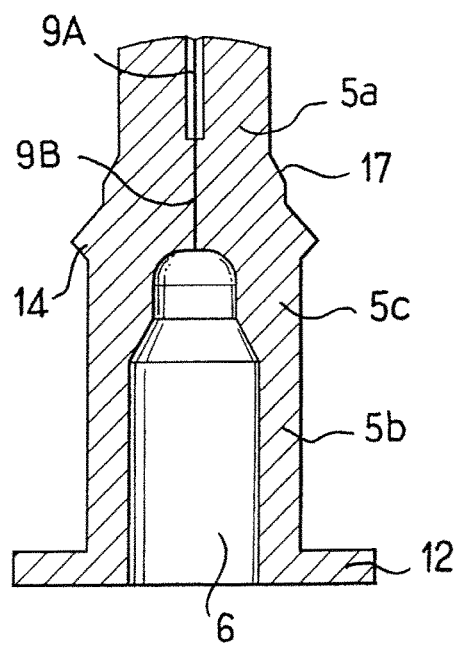
FIG_4

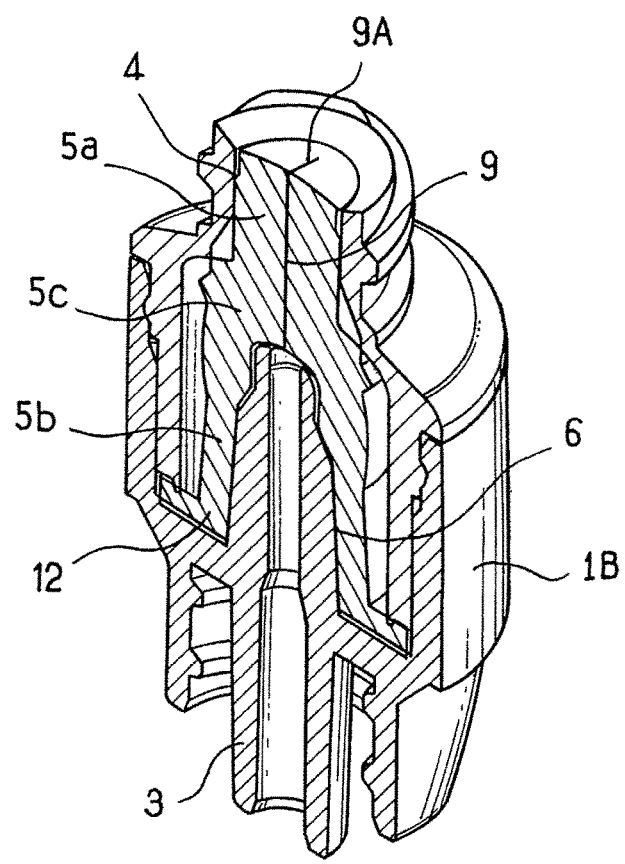
FIG_5

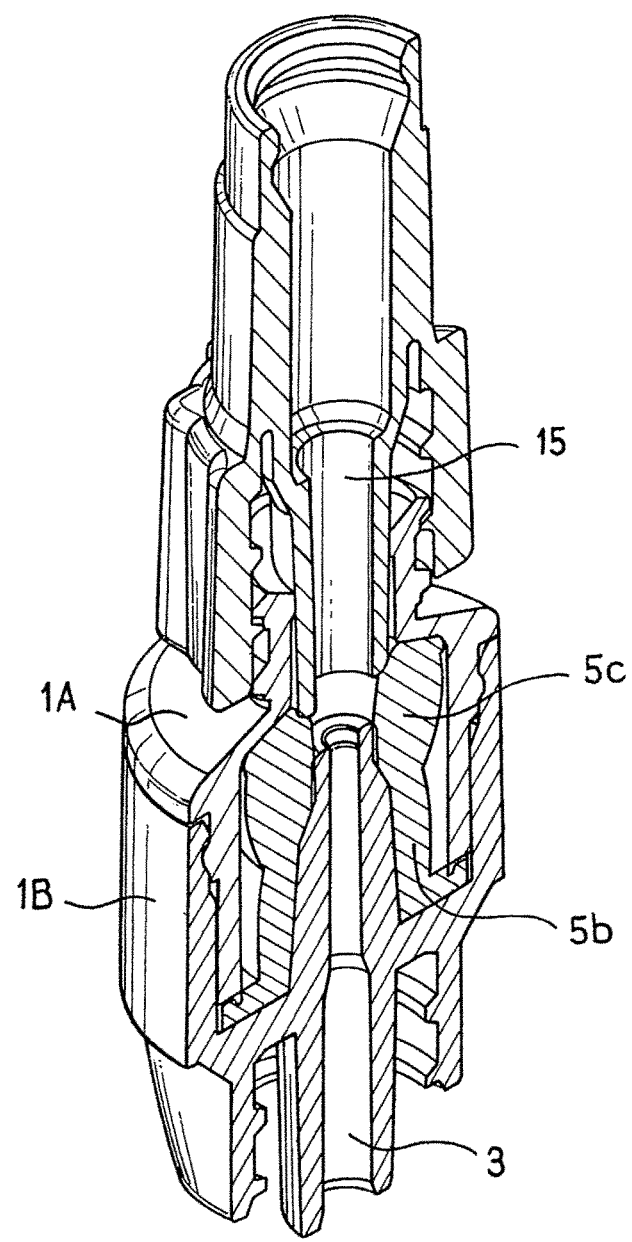
FIG_6

CONNECTOR FOR A ESTABLISHING A FLUID COMMUNICATION CONTROLLED BY A VALVE ESSENTIALLY USED IN THE FIELD OF MEDICINE

BACKGROUND OF THE INVENTION

This invention relates to a connector for establishing a fluid communication controlled by a valve, for use in the medical field in particular.

It relates more precisely to a connector comprising a rigid casing and an elastically deformable valve, the casing defining an elongated chamber along an axis of this chamber having a distal end and a proximal end, and being accessible, on the one hand, via a fixed end piece protruding axially into the distal end of the chamber and, on the other hand, by an axial channel formed at the proximal end of the chamber and into which a movable end piece can be inserted, and the valve being a single-piece, leak-proof walled tubular body made of an elastomeric material, which is housed inside the chamber, this valve having a distal end consisting of a tubular space into which said fixed end piece penetrates, and having an opposing end which is shaped in particular in order to form a plug inside said axial channel, this plug being slotted in order to communicate with said tubular space, the valve and the casing being shaped and dimensioned such that the plug is elastically movable between a closed position wherein it is in sealed contact with the wall of the channel and is laterally constrained by this wall so as to close the slot, and an open position wherein the plug is no longer laterally constrained by the wall of the channel so that the slot thereof can open.

Among the connectors of this type, the invention relates to those the valve of which is elastically deformable inside said chamber when same is pushed by the movable end piece inserted into said channel while creating a spring effect which enables same to resume the initial shape thereof when the movable end piece is withdrawn from said channel.

Connectors the valve of which has a spring-effect capacity are described in particular in the publications WO 97/21463, WO 98/50106, U.S. Pat. No. 6,068,011, EP 0 748 635, U.S. Pat. Nos. 5,676,346, 5,814,024 and 5,806,831.

The invention does in fact aim to provide a connector the valve of which is a laterally sealed single piece, which is elastically deformable with a spring effect, which surrounds the fixed end piece like the finger of a glove, and which meets several requirements:

the valve slot must open upon connection to the movable end piece, and completely expose the inside hole of the connected end piece, in order to enable a proper flow of the perfused liquid;

it must be possible to push the valve and immobilise the movable end piece (male Luer) with a moderate force of the order of 30 Newtons (#3 kg);

the valve must not create a dead volume inside the connector, which is synonymous with suction upon disconnection;

it must resist a strong liquid counter-pressure, which is possible with syringes and stopcock manifolds, for example;

it must be easy to clean, without any recesses or holes at the surface thereof, in order to not "hide" bacteria prior to connecting the movable end piece (male Luer); for this reason, it must always rise back up completely after disconnecting.

SUMMARY OF THE INVENTION

According to the invention, this is achieved with a connector characterized in that:

the spring-effect deformation capacity of the valve relates substantially to the plug and to a valve portion intermediate between the plug and said tubular space, the valve and the fixed end piece being shaped such that the valve is continuously clamped onto the fixed end piece without forming any significant dead volume inside said space, irrespective of the deformation of the valve, the fixed end piece and the valve are shaped such that the valve is held onto the fixed end piece without bending when pushed by the movable end piece, the valve slot consists of a proximal slot moulded such that the slot is open when the plug is outside of said channel, and is closed when the plug is laterally constrained by the wall of the channel, this proximal slot being followed by a perforated distal slot capable of connecting the moulded slot with said space when the slot is open, the perforated slot being closed when the plug is constrained inside the channel, the fixed end piece passing through the perforated slot and a portion of the moulded slot when the plug is outside of said channel, without the movable plug penetrating into the slot.

In preferred embodiments, the connector also has one or more of the following characteristics:

the fixed end piece has an exterior shoulder against which the valve abuts;

said shoulder is of a truncated cone shape;

said intermediate portion of the valve has a collar which cooperates with the wall of the chamber in order to prevent the valve from exiting from the connector when the valve rises up again under the influence of a counter-pressure;

at the level of said perforated slot, the valve has protruding stubs, which enter into said channel when the valve rises up inside the channel under the influence of a counter-pressure, and which act to compress the slot at this location.

DESCRIPTION OF THE DRAWINGS

A non-limiting example of a connector in accordance with the invention will be described hereinbelow with reference to the figures of the appending drawing, in which:

FIG. 1 is an axial schematic section of the connector at rest;

FIG. 2 is an axial schematic section of the connector in the connected state;

FIG. 3 is a perspective view of the valve prior to being mounted inside the casing of the connector;

FIG. 4 is an axial section of the valve prior to being mounted inside the casing of the connector;

FIG. 5 is an axially cut schematic perspective view of the valve in position and at rest inside the casing;

FIG. 6 is an axially cut schematic perspective view of the valve in position inside the casing after insertion of the movable end piece.

DESCRIPTION OF THE PREFERRED EMBODIMENT

The connector represented on the figures comprises
a casing 1 consisting of a female casing portion 1a and a male casing portion IB, which is fixed (screwed or clipped or glued or welded) inside the female portion, these two portions cooperating to form a chamber elongated along an axis, which is accessible at a distal end via a fixed axial end piece 3 integral with the female casing portion and which is accessible at the opposing proximal end thereof via an axial channel 4 formed inside the male casing portion;

an elastically deformable single-piece valve 5 made of silicon, for example, and having a laterally sealed wall, which is arranged inside said chamber, this valve consisting of a glove finger-like space 6 at a distal end 5b, which receives the fixed end piece 3, and a plug 5a at the opposing proximal end thereof, which is positioned inside the axial channel 4 so as to be sealed laterally and which is flush with the open end 8 of this channel.

The valve has a slot 9 a portion of which is moulded 9A and which is enclosed inside the axial channel when the valve is at rest inside the casing and a following portion 9B of which is split, e.g., with a scalpel, in order to connect the moulded portion with space 6.

Between the tubular space 6 and the plug 7, the valve 5 has an intermediate valve portion 10.

The valve is shaped so as to tightly clamp the fixed end piece 3, irrespective of the state of the valve, and this end piece has a truncated cone-shaped shoulder 11 close to the proximal end of space 6, against which the valve bears and which prevents it from slipping on the fixed end piece when pushed by the movable end piece.

The valve has a lateral collar 12 at the distal end thereof, which is applied against the base face of the chamber and held by the male casing portion which is screwed into the female casing portion.

The intermediate portion 5c of the valve is thicker than the portion 5b of the valve which defines space 6 and has a shoulder 14 and, above this shoulder, two stubs on each side of the cut slot.

In the unconstrained state (FIG. 3), the plug 5a has an approximately ellipsoidal straight section and the moulded slot 9A has an approximately ellipsoidal section, the major axes of the two ellipses being perpendicular. When the valve is constrained inside the proximal channel, the ellipsoidal section of the plug, via the contact of same with the wall of the channel, is forced to assume a circular shape and the moulded slot 9A is forced to close.

When the movable end piece 15 is inserted and pushed into the channel, it pushes the plug back into the chamber, out of the channel, whereby the moulded slot, which is no longer compressed, opens up by itself and whereby the cut slot is penetrated by the fixed end piece, while the intermediate portion 5c of the valve expands laterally inside the chamber while coming into contact with the upper wall 16 of the chamber. By bearing against the wall of the casing, the sheath stores up elastic energy in order to ensure the spring function and is incapable of closing upon itself owing to the presence of the fixed end piece.

At the transition between said channel and said chamber, the casing has a truncated cone-shaped straight section intended to ensure progressive deformation of the plug during insertion of the movable end piece into the channel or during withdrawal of this end piece.

When the valve rises up again, the two protruding stubs enter into the proximal channel of the casing and are compressed towards one another, thereby compressing the slot at this location and enabling a proper hold of the connector under counter-pressure.

The collar on the valve acts as a "shoulder". Under the influence of a counter-pressure, the valve is pushed upward (piston), the shoulder prevents same from being extruded into the preceding channel and from partially exiting from the connector, which would render any reconnection difficult.

The valve can only be deformed in the intermediate portion thereof, and the space inside the casing so enables it. When pushed by the movable male end piece, it flares out while at the same time being crushed onto the shoulder of the fixed tubular end piece. The seal is obtained by the impression of the male end piece inside the valve. The travel of the male end piece is variable, based on the geometry thereof (minimum/maximum tolerances), if the male Luer is mini, it is driven in considerably and becomes flush with the tubular end piece of the catch, otherwise there is a space between the male end piece and the fixed end piece, preferably a space equal to 1.7 mm at most.

The invention is not limited to the embodiments which have been described.

The invention claimed is:

1. Connector for establishing a fluid communication for use in the medical field, said connector comprising a rigid casing, defining an elongated chamber along an axis, said chamber having a distal end and a proximal end, the casing further having a truncated cone-shaped section transitioning from said proximal end of said chamber into an axial channel adjacent the proximal end of the chamber, adapted to receive a movable end piece, said casing having an upper wall at an interface between said axial channel and said chamber, said axial channel having a diameter smaller than a diameter of said distal end of said chamber, a fixed end piece protruding axially into the distal end of the chamber an elastically deformable valve, said valve being a single-piece, leak-proof walled tubular body made of an elastomeric material and housed inside the chamber, said valve having a distal end with an outer circumference and an inner tubular space filled by said fixed end piece, there being no dead volume in said tubular space between said fixed end piece and said valve, said valve having a proximal end with a convex contour, said proximal end of said valve forming a plug inside said axial channel, said plug having an axial slot comprising two stages, one of said stages being a proximal stage of said axial slot formed by a bore that is normally open, said proximal stage closing in response to movement of said plug from a position outside of said channel where said plug is not compressed to a position inside said channel where said plug is laterally constrained by the wall of the channel, and a distal stage of said axial slot formed by a split in said plug for connecting said proximal stage of said slot with said tubular space when said proximal stage of said slot is open, the plug being elastically movable between a closed position with said proximal end of said plug within said axial channel wherein it obstructs, and is in sealed contact with and laterally constrained by a wall of, said axial channel for closing the slot, and an open position within said chamber wherein the plug is no longer laterally constrained by the wall of the channel and the proximal end of the plug abuts against said upper wall, there being a space between said valve outer circumference and an inner wall of said chamber, said valve being sufficiently deformable for enlarging said slot and expanding said valve radially into said space between said valve outer circumference and said inner wall of said chamber sufficiently to prevent obstruction of said axial channel for permitting said movable end piece to penetrate said slot, and to resume the initial shape thereof when the movable end piece is withdrawn from said slot.

2. Connector of claim 1, wherein the fixed end piece (3) has an exterior shoulder (11) against which the valve abuts.

3. Connector of claim 2, wherein said shoulder (11) is of a truncated cone shape.

4. Connector as claimed in one of claims 1 to 3, an intermediate valve portion (5*c*) of which has a collar (14) which cooperates with the inner wall of the chamber in order to prevent the valve from exiting from the connector when the valve rises up again under the influence of a counter-pressure.

5. Connector as claimed in claim 1, of which the valve, at a level of said split distal slot portion, has protruding stubs (17), which enter into said channel when the valve rises up inside the channel under the influence of a counter-pressure, and which act to compress the slot at this location.

6. Connector as claimed in claim 1, the casing of which consists of a female casing portion (1A) inside which a male casing portion (1B) is fixed, and the valve (5) has a collar (12) at the distal end thereof, which is clamped around the fixed end piece between these two portions.

7. Connector as claimed in claim 1 wherein said bore is ellipsoid in section.

\* \* \* \* \*